(12) United States Patent
Trofast

(10) Patent No.: US 6,287,540 B1
(45) Date of Patent: *Sep. 11, 2001

(54) FORMULATION FOR INHALATION

(75) Inventor: Jan Trofast, Lund (SE)

(73) Assignee: Astra Aktiebolag, Södertälje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/431,916

(22) Filed: Nov. 2, 1999

Related U.S. Application Data

(63) Continuation-in-part of application No. 09/004,902, filed on Jan. 9, 1998, now Pat. No. 6,030,604.

(30) Foreign Application Priority Data

Jan. 9, 1998 (SE) ................................... 9700135

(51) Int. Cl.⁷ .......................... A61K 9/14; A61K 31/56; A61K 31/58; A61K 31/135
(52) U.S. Cl. .......................... 424/46; 514/171; 514/174; 514/653; 514/826
(58) Field of Search .............................. 424/46; 514/171, 514/174, 653, 826

(56) References Cited

U.S. PATENT DOCUMENTS

| | | | |
|---|---|---|---|
| 4,199,578 | 4/1980 | Stevenson | 424/240 |
| 4,414,209 | 11/1983 | Cook et al. | 424/243 |
| 4,524,769 | 6/1985 | Wetterlin | 128/203.15 |
| 4,534,345 | 8/1985 | Wetterlin | 128/203.15 |
| 4,590,206 | 5/1986 | Forrester et al. | 514/456 |
| 5,192,548 | 3/1993 | Velasquez et al. | 424/443 |
| 5,355,872 | 10/1994 | Riggs et al. | 128/200.21 |
| 5,474,759 | 12/1995 | Fassberg et al. | 424/45 |
| 5,503,869 | 4/1996 | Van Oort | 427/2.14 |
| 5,538,999 | 7/1996 | Clark et al. | 514/653 |
| 5,551,489 | 9/1996 | Trofast et al. | 141/18 |
| 5,562,923 | 10/1996 | Trofast et al. | 424/489 |
| 5,614,514 | 3/1997 | Axelsson et al. | 514/174 |
| 5,628,307 | 5/1997 | Clark et al. | 128/203.15 |
| 5,637,620 | 6/1997 | Trofast et al. | 514/630 |
| 5,647,347 | 7/1997 | Van Oort | 128/203.15 |
| 5,654,007 | 8/1997 | Johnson et al. | 424/489 |
| 5,655,523 | 8/1997 | Hodson et al. | 128/315 |
| 5,674,860 | 10/1997 | Carling et al. | 514/171 |
| 5,674,861 | 10/1997 | Anderson et al. | 514/174 |
| 5,700,410 | 12/1997 | Nakamichi et al. | 264/122 |
| 5,709,884 | 1/1998 | Trofast et al. | 424/489 |
| 5,736,124 | 4/1998 | Akehurst et al. | 424/45 |
| 6,030,604 | * 2/2000 | Trofast | 424/46 |

FOREIGN PATENT DOCUMENTS

| | | |
|---|---|---|
| WO/93/11773 | 6/1993 | (WO) . |
| WO/9505805 | 3/1995 | (WO) . |
| WO/95/09616 | 4/1995 | (WO) . |
| WO/98/15280 | 4/1998 | (WO) . |

* cited by examiner

Primary Examiner—Kevin E. Weddington
(74) Attorney, Agent, or Firm—Fish & Richardson P.C.

(57) ABSTRACT

A dry powder composition comprising one more potent pharmaceutically active substances and a carrier substance, all of which are in finely divided form, wherein the formulation has a poured bulk density of from 0.28 to 0.38 g/ml is useful in the treatment of respiratory disorders.

16 Claims, No Drawings

FORMULATION FOR INHALATION

This Application is a CIP of Ser. No. 09/004,902 filed Jan. 9, 1998, U.S. Pat. No. 6,030,604.

FIELD OF THE INVENTION

The present invention provides a new pharmaceutical formulation, its preparation and its use.

BACKGROUND TO THE INVENTION

Potent drugs for administration by inhalation are generally formulated in association with carriers such as lactose because of the problem of preparing accurate doses. When such drugs are diluted, variations in the weight of the formulation result in a smaller drug dosage rate compared with when they are not diluted. These formulations have generally consisted of coarse particles of the carrier with fine particles of the drug, which combination is generally known as an ordered mixture.

The invention provides an improved formulation which, in systems designed to imitate inhalation has been found to give an improved dispersion of the drug.

DESCRIPTION OF THE INVENTION

According to the invention there is provided a dry powder composition comprising one or more potent pharmaceutically active substances and a carrier substance, all of which are in finely divided form, wherein the formulation has a poured bulk density of from 0.28 to 0.38 g/ml, preferably from 0.30 to 0.36 g/ml. The poured bulk density according to the present invention is measured using known techniques, for example those described in "Powder testing guide: Methods of measuring the physical properties of Bulk powders" L. Svarovsky, Elsevier Applied Science 1987, pp 84–86.

A potent pharmaceutically active substance suitable for use in the invention is, for example, an antiarrhythmic drug, tranquilizer, cardiac glycoside, hormone, hypertensive drug, antidiabetic or anticancer drug, sedative or analgesic drug, antibiotic, antirheumatic drug, immunotherapy, antifungal or antihypotension drug, vaccine, antiviral drug, protein (e.g. insulin), peptide, vitamin, or a cell surface receptor blocker. It is preferably a glucocorticosteroid, particularly one which is metabolized rapidly, for example beclomethasone dipropionate (BDP), beclomethasone monopropionate (BMP), flunisolide, triamcinolone acetonide, fluticasone propionate, ciclesonide, budesonide, rofleponide or derivatives thereof, momethasone, tipredane, RPR 106541 and/or a β2-agonist such as terbutaline, salbutamol, formoterol, salmeterol, TA 2005, pircumarol or a pharmaceutically acceptable salt thereof; and/or a prophylactic agent such as sodium chromoglycate or nedocromil sodium.

Suitable physiologically acceptable salts include acid addition salts derived from inorganic and organic acids, for example the chloride, bromide, sulphate, phosphate, maleate, fumarate, tarrate, citrate, benzoate, 4-methoxybenzoate, 2- or 4-hydroxybenzoate, 4-chlorobenzoate, p-toluenesulphonate, methanesulphonate, ascorbate, acetate, succinate, lactate, glutarate, gluconate, tricarballylate, hydroxynaphthalene-carboxylate or oleate salts or solvates thereof.

The carrier substance is preferably a mono-, di- or polysaccharide, a sugar alcohol or another polyol. Suitable carriers are, for example, lactose, glucose, raffinose, melezitose, lactitol, maltitol, trehalose, sucrose, mannitol; and starch. Lactose is particularly preferred, especially in the form of its monohydrate.

The ingredients of the formulation according to the invention must both be in a finely divided form, i.e. their mass median diameter should generally be less than 10 μm, preferably from 1 to 7 μm, as measured by a laser diffraction instrument or a coulter counter. The ingredients may be produced in the desired particle size using methods known to those of skill in the art, e.g. milling, micronization or direct precipitation.

The combination of budesonide and formoterol is particularly preferred. Formoterol is preferably used in the form of its fumarate, especially the dihydrate.

When the one or more potent pharmaceutically active substances used in the invention are formoterol and budesonide, the molar ratio of formoterol to budesonide in the composition of the invention is preferably from 1:2500 to 12:1, more preferably from 1:555 to 2:1, most preferably from 1:133 to 1:6. The composition according to the invention is preferably formulated to provide a daily dose of formoterol of from 2 to 120 nmol (more preferably from 7 to 70 nmol). When formoterol is used in the form of formoterol fumarate dihydrate, the composition is preferably formulated to provide a daily dose of formoterol fumarate dihydrate of from 1 to 50 μg, more preferably from 3 to 30 μg. The composition according to the invention is preferably formulated to provide a daily dose of budesonide of from 45 to 2200 μg, more preferably from 65 to 1700 μg.

More preferably the composition of the invention comprises, as a unit dose, 6 μg of formoterol fumarate dihydrate and 100 μg of budesonide, or 4.5 μg of formoterol fumarate dihydrate and 80 μg of budesonide, either of which can be administered up to four times a day. Alternatively the composition of the invention comprises, as a unit dose, 12 μg of formoterol fumarate dihydrate and 200 μg of budesonide, or 9 μg of formoterol fumarate dihydrate and 160 μg of budesonide, either of which is administered once or twice a day. Most preferably the composition used in the invention comprises, as a unit dose, 6 μg of formoterol fumarate dihydrate and 200 μg of budesonide, or 4.5μg of formoterol fumarate dihydrate and 160 μg of budesonide, either of which is administered up to four times a day. Alternatively the composition of the invention comprises, as a unit dose, 12 μg of formoterol fumarate dihydrate and 400 μg of budesonide, or 9 μg of formoterol fumarate dihydrate and 320 μg of budesonide, either of which is administered once or twice a day.

According to the invention there is further provided a process for preparing a composition according to the invention which comprises (a) micronizing the one or more potent pharmaceutically active substances and the carrier substance;

(b) optionally conditioning the product; and (c) spheronizing until the desired bulk density is obtained.

The process preferably rher comprises a low energy remicronization step after step (b).

The formulation according to the invention may be made by conventional techniques known per se. Such production processes generally comprise micronizing the ingredients to the required size, removing any amorphous areas on the particles obtained by, for example, the methods described in WO 92/18110 or WO 95/05805 and then agglomerating, spheronizing and sieving the powder obtained. The size of the agglomerates obtained is preferably in the range of from 100 to 2000 μm, more preferably is from 100 to 800 μm. The bulk density of the formulation produced may be adjusted by varying the components and the process empirically, for example the bulk density can be increased by lengthening the time in which the particles are tumbled in a spheronizing device.

In solid-solid mixing, one of the most important features is to ensure content uniformity. The major problem encountered in the powder mixing of fine powders is the inability of mixers to break down powder agglomerates. It has been found that a remicronization step after the conditioning step of the fine powder with low energy input is advantageous. It should generally be carried out using enough energy to break down powder agglomerates but not with so much energy that the size of the particles themselves is affected. Such a step gives a composition wherein the active substance and carrier substance are substantially uniformly distributed, having for example a relative standard deviation of less than 3% (preferably less than 1%) and does not disturb the crystallinity of the fine particles.

The formulation according to the invention may be administered using any known dry powder inhaler, for example the inhaler may be a single or a multi dose inhaler, and may be a breath actuated dry powder inhaler, for example Turbuhaler (trade mark). The invention further provides use of a composition according to the invention in the manufacture of a medicament for use in therapy. The composition according to the invention is useful in the treatment of respiratory disorders, particularly asthma The invention also provides a method of treating a patient suffering from a respiratory disorder which comprises administering to the patient a therapeutically effective amount of a composition according to the invention.

The invention is illustrated, but not limited, by reference to the following Examples.

EXAMPLE 1

0.0315 Parts of formoterol flimarate dihydrate and 2.969 parts of lactose monohydrate are mixed in a tumbling mixer (Turbula) to an evenly distributed mixture, whereafter the mixture is micronized in a spiral jet mill using a pressure and feeding rate suitable to obtain a particle size of less than 3 $\mu$m (mass median diameter as measured by a coulter counter). The micronized articles were then treated using the method disclosed in WO 95/05805 to remove amorphous regions in their crystal structure. The powder was then agglomerated by feeding the powder into a twin screw feeder (K-Tron), sieving in an oscillating sieve (0.5 mm mesh size), spheronizing in a rotating pan with a peripheral speed of 0.5 m/s for 4 minutes and then sieving again using the same sieve, thens spheronizing once more for 6 minutes before final sieving (mesh size 1.0 mm) giving a powder with a bulk density of 0.32 g/ml.

EXAMPLE 2

Example 1 was repeated but the powder was remicronized in a spiral jet mill at a lower pressure (about 1 bar) after micronization and conditioning such that the step of treating the particles in the manner described in WO 95/05805 was not required giving a powder with a bulk density of 0.32 g/ml.

EXAMPLE 3

9 Parts of budesonide and 91 parts of lactose monohydrate were micronized separately in a spiral jet mill at a pressure of about 6–7 bars to give a particle size of less than 3 $\mu$m before being mixed thoroughly in a Turbula mixer. Before mixing, the lactose monohydrate powder was conditioned according to the method described in WO 95/05805. The mixture was remicronized in a spiral jet mill at a pressure of only about 1 bar to obtain a uniform mixture. The powder was then agglomerated and spheronized as described in Example 1 to obtain a bulk density of 0.35 g/ml.

EXAMPLE 4

60 Parts of terbutaline sulphate were micronized to a mass medium diameter of less than 2 $\mu$m in a Alpin mill 100AFG and thereafter conditioned according to the method described in U.S. Pat. No. 5562923. 40 Parts of lactose monohydrate were micronized (Alpin mill 100AFG) down to a mass medium diameter of less than 3 $\mu$m and thereafter conditioned according to the method described in WO 95/05805. The micronized and conditioned terbutaline sulphate and lactose monohydrate were mixed thoroughly in a Turbula mixer. The mixture was remicronized in a spiral jet mill at a pressure of only about 1 bar to obtain an evenly distributed mixture. The powder was then agglomerated and spheronized as described in Example 1 to obtain a bulk density of 0.28 g/ml.

EXAMPLE 5

Example 4 was repeated with 30 parts of terbutaline sulphate and 70 parts of lactose monohydrate to give a powder with a bulk density of 0.31 g/ml.

EXAMPLE 6

5.2 Parts of formoterol fumarate dihydrate and 896.8 parts of lactose monohydrate were mixed in a tumbling mixer to an evenly distributed mixture, whereafter the mixture was micronized in a spiral mill using a pressure and feeding rate suitable to obtain a particle size of less than 3 $\mu$m (mass medium diameter as measured by a coulter counter). The micronized particles were then treated using the method described in WO 95/05805 to remove amorphous regions in their crystal structure. 98 parts of micronized budesonide were added and the mixture was remicronized at a lower pressure in a spiral jet mill to a homogenous mixture. The powder was then agglomerated by feeding into a screw feeder (K-Tron), sieved in an oscillating sieve (0.5 mm mesh size), spheronized in a rotating pan with a speed of 23 rpm for 10 minutes, then sieved again (0.5 mm mesh size), spheronized once more before being finally sieved (0.8 mm mesh size) to give a powder with a bulk density of 0.34 g/ml.

EXAMPLE 7

Example 6 was repeated with identical conditions but using 5.2 parts of micronized formoterol fumarate dihydrate, 798.8 parts of micronized lactose monohydrate and 196 parts of micronized budesonide. The bulk density obtained was 0.34 g/ml.

What is claimed is:

1. A dry powder composition comprising one potent therapeutically active substance and a carrier substance, both of which are in finely divided form, wherein the composition has a poured bulk density of from 0.28 to 0.38 g/ml and said finely divided therapeutically active substance and said finely divided carrier substance are substantially uniformly distributed throughout the composition.

2. The composition according to claim 1, wherein the poured bulk density of the composition is from 0.30 to 0.36 g/ml.

3. The composition according to claim 1, for use in the treatment of a respiratory disorder.

4. The composition according to claim 1, wherein the potent therapeutically active substance is selected from the group consisting of glucocorticosteroids, β2-agonists and prophylactic agents.

5. The composition according to claim 4, wherein the glucocorticosteroid is selected from the group consisting of beclomethasone dipropionate (BDP), beclomethasone monopropionate (BMP), flunisolide, triamcinolone acetonide, fluticasone propionate, ciclesonide, momethasone, tipredane, RPR 106541, rofleponide and derivatives thereof.

6. The composition according to claim 4, wherein the β2-agonist is selected from the group consisting of salbutamol, salmeterol, TA 2005, pircumarol and pharmaceutically acceptable salts thereof.

7. The composition according to claim 4, wherein the prophylactic agent is selected from the group consisting of sodium chromoglycate and nedocromil sodium.

8. The composition according to claim 1, wherein the carrier substance is selected from the group consisting of monosaccharides, disaccharides, polysaccharides and polyols.

9. The composition according to claim 8, wherein the disaccharide is lactose.

10. The composition according to claim 9, wherein the disaccharide is lactose monohydrate.

11. The composition according to claim 1, wherein the therapeutically active substance and carrier substance have a mass median diameter of less than 10 μm.

12. The composition according to claim 11, wherein said mass median diameter is from 1 to 7 μm.

13. A process for preparing a composition according to claim 10, comprising (a) micronizing, either separately or together, the potent therapeutically active substance and the carrier substance;

(b) either before, during, or after step (a), mixing the potent therapeutically active substance and the carrier substance, both of which are in finely divided form, until a substantially uniform mixture is obtained; and (c) spheronizing said substantially uniform mixture until a poured bulk density of from 0.28 to 0.38 g/ml is obtained.

14. A process according to claim 13, further comprising conditioning the micronized substances.

15. A process according to claim 14, wherein the conditioning step is performed before the spheronization step.

16. A process according to claim 14, further comprising a low energy remicronization step after the conditioning step.

* * * * *

UNITED STATES PATENT AND TRADEMARK OFFICE
CERTIFICATE OF CORRECTION

| | | |
|---|---|---|
| PATENT NO. | : 6,287,540 B1 | Page 1 of 1 |
| APPLICATION NO. | : 09/431916 | |
| DATED | : September 11, 2001 | |
| INVENTOR(S) | : Jan Trofast | |

It is certified that error appears in the above-identified patent and that said Letters Patent is hereby corrected as shown below:

Title page, Item (63) Related U.S. Application Data,
replace "continuation-in-part" with --continuation--.

Title page, Item (30) Foreign Application Priority Data,
replace "Jan. 9, 1998 (SE)................ 9700135"
with --Jan. 20, 1997 (SE)................ 9700135-8--.

Column 1, line 3, replace "CIP" with --continuation--.

Column 1, line 16, after "dosage", insert --variation--.

Column 1, line 57, replace "tarrate" with --tartrate--.

Column 2, line 56, replace "rher" with --further--.

Column 3, line 42, replace "articles" with --particles--.

Column 6, line 7, replace "claim 10" with --claim 1--.

Signed and Sealed this

Eighth Day of April, 2008

JON W. DUDAS
*Director of the United States Patent and Trademark Office*